(12) United States Patent
Yamagata et al.

(10) Patent No.: US 7,869,640 B2
(45) Date of Patent: *Jan. 11, 2011

(54) MEDICAL IMAGE PROCESSING APPARATUS AND MEDICAL IMAGE PROCESSING METHOD

(75) Inventors: Hitoshi Yamagata, Otawara (JP); Sumiaki Matsumoto, Kobe (JP); Yoshiharu Ohno, Kobe (JP)

(73) Assignees: National University Corporation Kobe University, Kobe-shi (JP); Toshiba Medical Systems Corporation, Otawara-shi (JP)

( * ) Notice: Subject to any disclaimer, the term of this patent is extended or adjusted under 35 U.S.C. 154(b) by 540 days.

This patent is subject to a terminal disclaimer.

(21) Appl. No.: 12/015,107

(22) Filed: Jan. 16, 2008

(65) Prior Publication Data

US 2008/0170771 A1 Jul. 17, 2008

(30) Foreign Application Priority Data

Jan. 16, 2007 (JP) ............................. 2007-007387

(51) Int. Cl.
*G06K 9/00* (2006.01)
*A61B 6/00* (2006.01)

(52) U.S. Cl. ...................... 382/128; 382/274; 378/21

(58) Field of Classification Search ................ 382/100, 382/128, 129, 130, 131, 132, 133, 134, 154, 382/168, 181, 189, 203, 224, 232, 255, 260, 382/274, 276, 285, 305, 312; 707/102; 378/4, 378/21; 600/425

See application file for complete search history.

(56) References Cited

U.S. PATENT DOCUMENTS

| 6,738,499 | B1 * | 5/2004 | Doi et al. ..................... 382/128 |
| 2003/0016850 | A1 * | 1/2003 | Kaufman et al. ............ 382/128 |
| 2005/0207630 | A1 * | 9/2005 | Chan et al. .................. 382/131 |
| 2007/0230763 | A1 * | 10/2007 | Matsumoto et al. ......... 382/131 |
| 2007/0286469 | A1 * | 12/2007 | Yamagata et al. ........... 382/131 |

(Continued)

FOREIGN PATENT DOCUMENTS

WO WO 2006/093085 A1 9/2006

OTHER PUBLICATIONS

David S. Paik, et al., "Surface Normal Overlap: A Computer-Aided Detection Algorithm With Application to Colonic Polyps and Lung Nodules in Helical CT", IEEE Transactions on Medical Imaging, vol. 23, No. 6, Jun. 2004, pp. 661-675.

(Continued)

*Primary Examiner*—Seyed Azarian
(74) *Attorney, Agent, or Firm*—Oblon, Spivak, McClelland, Maier & Neustadt, L.L.P.

(57) ABSTRACT

A medical image processing apparatus includes an acquisition unit which acquires an anatomical malignant grade of an abnormality candidate region that is possibly an anatomical abnormality included in an image showing the inside of a subject based on a candidate region characteristic amount indicative of characteristics concerning the abnormality candidate region and a peripheral region characteristic amount indicative of characteristics concerning a peripheral region continuous with the abnormality candidate region in the image, a determination unit which determines an examination policy or a treatment policy with respect to the abnormality candidate based on the malignant grade, and a presentation unit which presents the examination policy or the treatment policy determined by the determination unit to a user.

10 Claims, 10 Drawing Sheets

U.S. PATENT DOCUMENTS

2008/0170771 A1* 7/2008 Yamagata et al. ........... 382/128

OTHER PUBLICATIONS

Kenji Suzuki, et al., "Computer-Aided Diagnostic Scheme for Distinction Between Benign and Malignant Nodules in Thoracic Low-Dose CT by Use of Massive Training Artificial Neural Network", IEEE Transactions on Medical Imaging, vol. 24, No. 9, Sep. 2005, pp. 1138-1150.

U.S. Appl. No. 12/407,087, filed Mar. 19, 2009, Matsumoto et al.

Sumiaki Matsumoto, et al., "Diminution index: A novel 3D feature for pulmonary nodule detection", International Congress Series, vol. 1281, XP005081826, ISSN: 0531-5131, 2005, pp. 1093-1098.

Yoshito Mekada Y., et al., "A Concentration Index for Analyzing Three-Dimensional Line Patterns and Its Application to X-ray CT Images", Electronics and Communication in Japan, Part 3, vol. 81, No. 7, XP000832211, ISSN: 1042-0967, 1998, pp. 7-17.

Daniel M. Libby, et al., "Managing the small Pulmonary Nodule Discovered by CT", Chest, vol. 125, No. 4, XP007904678, 2004, pp. 1522-1529.

U.S. Appl. No. 12/187,866, filed Aug. 7, 2008, Yamagata, et al.

* cited by examiner

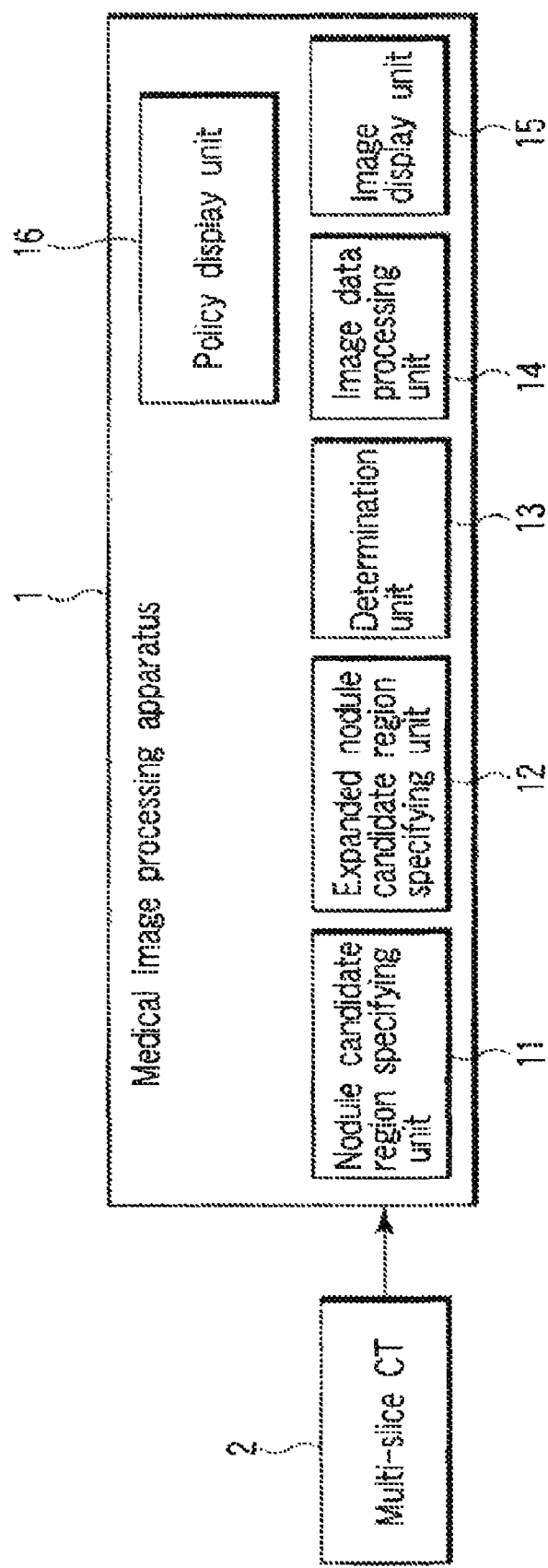
F I G. 1

| Malignancy grade (indicated in %) | Presentation contents of examination/treatment policy |
|---|---|
| 0 | Reexamination with CT after 12 months |
| 10 | Reexamination with CT after 6 months |
| 20 | Periodic examination with CT every 3 months |
| 40 | PET examination |
| 60 | Biopsy examination |
| 80 | Biopsy examination + extirpative surgery |
| 100 | Extirpative surgery |

| Malignant grade related to connected blood vessel (indicated in %) \ Malignant grade related to nodule (indicated in %) | 0 | 25 | 50 | 100 |
|---|---|---|---|---|
| 0 | Reexamination with CT after 12 months | Reexamination with CT after 6 months | Periodic examination with CT every 3 months | PET |
| 25 | Reexamination with CT after 12 months | Reexamination with CT after 6 months | PET | Biopsy examination |
| 50 | Reexamination with CT after 6 months | PET | Biopsy examination | Biopsy examination + extirpative surgery |
| 100 | Periodic examination with CT every 3 months | Biopsy examination | Biopsy examination + extirpative surgery | Extirpative surgery |

F I G. 9

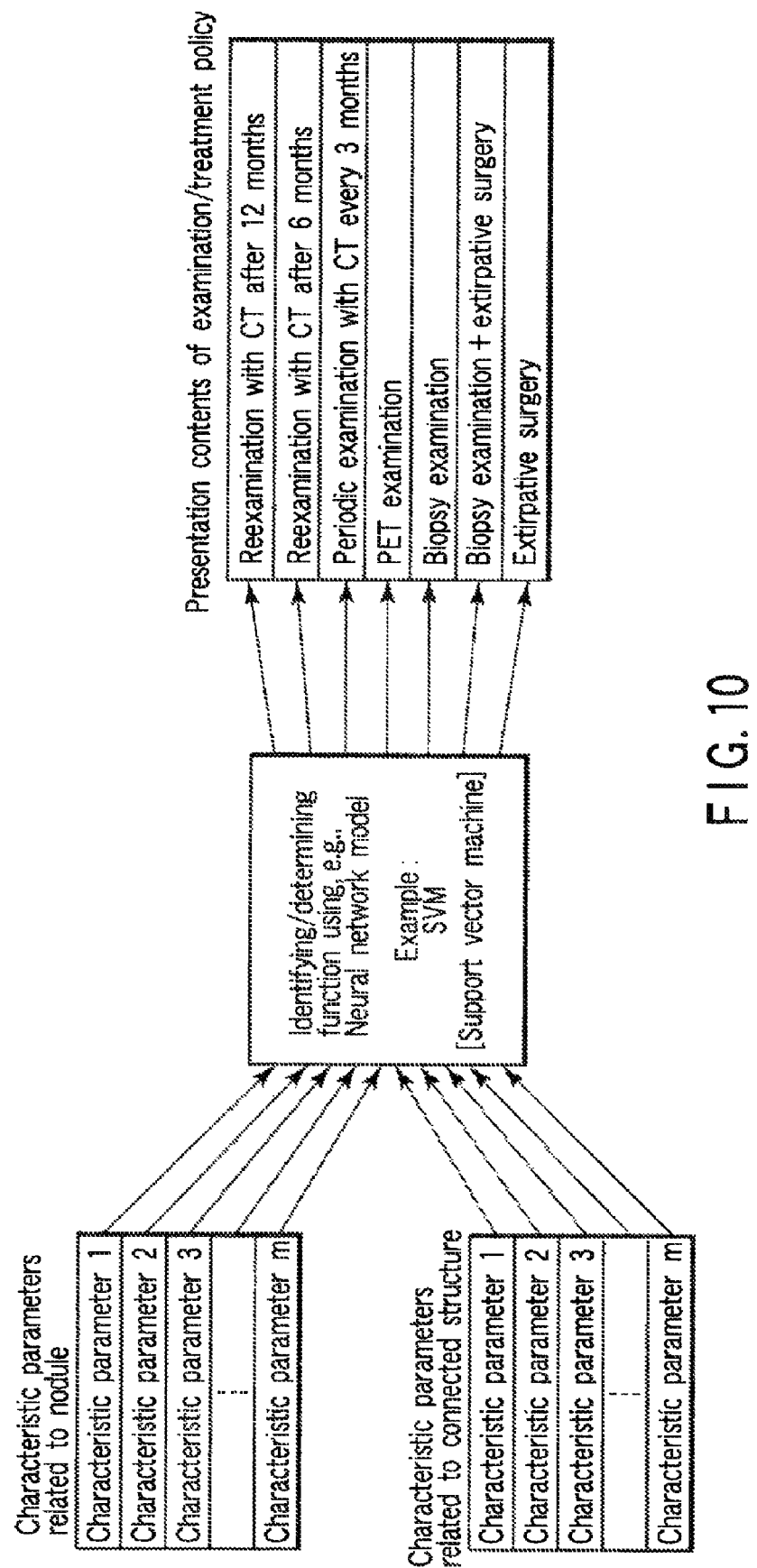
F I G. 10

MEDICAL IMAGE PROCESSING APPARATUS AND MEDICAL IMAGE PROCESSING METHOD

CROSS-REFERENCE TO RELATED APPLICATIONS

This application is based upon and claims the benefit of priority from prior Japanese Patent Application No. 2007-007387, filed Jan. 16, 2007, the entire contents of which are incorporated herein by reference.

BACKGROUND OF THE INVENTION

1. Field of the Invention

The present invention relates to a medical image processing apparatus and a medical image processing method that assist a diagnosis of an anatomic abnormality, e.g., a nodular abnormality or a wen abnormality, based on a three-dimensional image collected by using a medical diagnostic imaging modality, e.g., an X-ray computer tomographic apparatus, an X-ray diagnostic apparatus, a magnetic resonance diagnostic apparatus, or an ultrasonic diagnostic apparatus.

2. Description of the Related Art

At the present day, a lung cancer heads a list of malignant deaths and goes on increasing in Japan. Therefore, a social demand for early detection is strong with respect to the lung cancer like precaution as a countermeasure for smoking. In each municipalities in Japan, a lung cancer examination based on a chest plain radiograph and a sputum cytodiagnosis is carried out. However, a report "Study Group Concerning Cancer Examination Effectiveness Evaluation" issued from Health and Welfare Ministry in Japan in 1998 concludes that a current lung cancer examination has effectiveness but it is small. An X-ray computer tomography (which will be referred to as a CT hereinafter) can readily detect a lung field type lung cancer as compared with a chest plain radiograph, but it was not able to be used for examination since its imaging time is long before 1990 when a helical scanning type CT (helical CT) appeared. However, soon after the helical CT appeared, a method of using a relatively low X-ray tube current to perform imaging for a reduction in radiation exposure (which will be referred to as a low-dose helical CT hereinafter) was developed, and a pilot study of a lung cancer examination using this method was carried out in Japan and the United States. As a result, a fact that the low-dose helical CT has a lung cancer detection rate greatly higher than that of the chest plain radiograph was proved.

On the other hand, a time required for imaging by the helical CT is kept being reduced due to an increase CT detectors after 1998. The latest multi-detector helical CT, an entire lung can be imaged in 10 seconds with a substantially isotropic resolution that is less than 1 mm. Such a CT technology innovation develops a potentiality of enabling detection of a lung cancer when it is smaller. However, the multi-detector helical CT also has a problem of considerably increasing a burden on diagnosing reading since it generates several-hundreds images per scanning operation.

Based on such a background, it is widely recognized that a computer assisted diagnosis (which will be referred to as a CAD hereinafter) using a computer to avoid an oversight of a lung cancer is required for the low-dose helical CT to be established as a lung cancer examination method.

Since a small lung cancer in a lung field appears as a nodular abnormality in a CT image, automatic detection of such an abnormality is an important theme, and various studies have been conducted since the 1990's (see, e.g., "David S. Paik and seven others, "Surface Normal Overlap: A Computer-aided Detection Algorithm with Application to Colonic Polyps and Lung Nodules in Helical CT", IEEE Transactions on Medical Imaging, Vol. 23, No. 6, Jun. 2004, pp. 661-675").

Now, it has been reported that many nodule candidates detected by a CAD are benign. Therefore, several techniques have been introduced because it is recognized that computer-aided differential diagnosis for revealing whether a nodule candidate is benign or malignant is also important (see, e.g., Kenji Suzuki and three others, "Computer-Aided Diagnostic Scheme for Distinction Between Benign and Malignant Nodules in Thoracic Low-dose CT by Use of Massive Training Artificial Neural Network", IEEE TRANSACTION ON MEDICAL IMAGING, VOL. 24, NO. 9, Sept. 2005, pp. 1138-1150).

Automatic detection of a pulmonary nodule in a CT image takes an approach of extracting a region as a candidate for a nodule (which will be referred to as a nodule candidate region hereinafter) by any method, obtaining a plurality of characteristic amounts characterizing this nodule candidate region, and determining whether the nodule candidate region is a nodule based on these characteristic amounts. However, since characteristics of a nodule are similar to those of a part of a lung blood vessel, the nodule and the lung blood vessel cannot be accurately discriminated from each other based on characteristic amounts charactering the nodule candidate region in some cases.

Under such circumstances, a final judgment on whether the nodule candidate region is a nodule is still committed to medical doctors. Usually, this judgment is made based on observation of an image showing a cross section. However, in this method, since a three-dimensional shape cannot be immediately recognized discriminating the nodule from the lung blood vessel takes time in some cases, and it cannot be said that an efficiency of the judgment is necessarily good.

As explained above, an examination policy or a treatment policy concerning an abnormality candidate region has been conventionally determined based on a physician's personal opinions, and hence it is not necessarily determined adequately.

BRIEF SUMMARY OF THE INVENTION

Under the circumstances, adequately determining an appropriate examination/treatment policy concerning an abnormality candidate region to support medical diagnostic imaging by a physician has been demanded.

According to a first aspect of the present invention, there is provided a medical image processing apparatus comprising: an acquisition unit which acquires an anatomical malignancy grade of an abnormality candidate region that is possibly an anatomical abnormality included in an image showing the inside of a subject based on a candidate region characteristic amount indicative of characteristics concerning the abnormality candidate region and a peripheral region characteristic amount indicative of characteristics concerning a peripheral region continuous with the abnormality candidate region in the image; a determination unit which determines an examination policy or a treatment policy with respect to the abnormality candidate based on the malignancy grade; and a presentation unit which presents the examination policy or the treatment policy determined by the determination unit to a user.

According to a second aspect of the present invention, there is provided a medical image processing apparatus comprising: an acquisition unit which acquires an anatomical malignancy grade of an abnormality candidate region that is possibly an anatomical abnormality included in an image showing the inside of a subject; a determination unit which determines an examination policy or a treatment policy with respect to the abnormality candidate based on the malignancy grade; and a presentation unit which presents the examination policy or the treatment policy determined by the determination unit.

According to a third aspect of the present invention, there is provided a medical image processing method comprising: acquiring an anatomical malignancy grade of an abnormality candidate region that is possibly an anatomical abnormality included in an image showing the inside of a subject based on a candidate region characteristic amount indicative of characteristics concerning the abnormality candidate region and a peripheral region characteristic amount indicative of characteristics concerning a peripheral region continuous with the abnormality candidate region in the image; determining an examination policy or a treatment policy with respect to the abnormality candidate based on the malignancy grade; and presenting the determined examination policy or treatment policy to a user.

According to a fourth aspect of the present invention, there is provided a medical image processing method comprising: acquiring an anatomical malignancy grade of an abnormality candidate region that is possibly an anatomical abnormality included in an image showing the inside of a subject; determining an examination policy or a treatment policy with respect to the abnormality candidate based on the malignancy grade; and presenting the determined examination policy or treatment policy to a user.

Advantages of the invention will be set forth in the description which follows, and in part will be obvious from the description, or may be learned by practice of the invention. Advantages of the invention may be realized and obtained by means of the methods and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a view showing a structure of a medical image processing apparatus 1 according to an embodiment;

FIG. 9 is a view showing an example of a matrix relationship table showing a relationship between two malignancy grades of characteristics parameters related to nodule connected blood vessel and characteristic parameters related to nodule partial, and an examination policy and a treatment policy;

FIG. 10 is a view showing a modification of determination processing for an examination policy and a treatment policy;

DETAILED DESCRIPTION OF THE INVENTION

Figure 2:
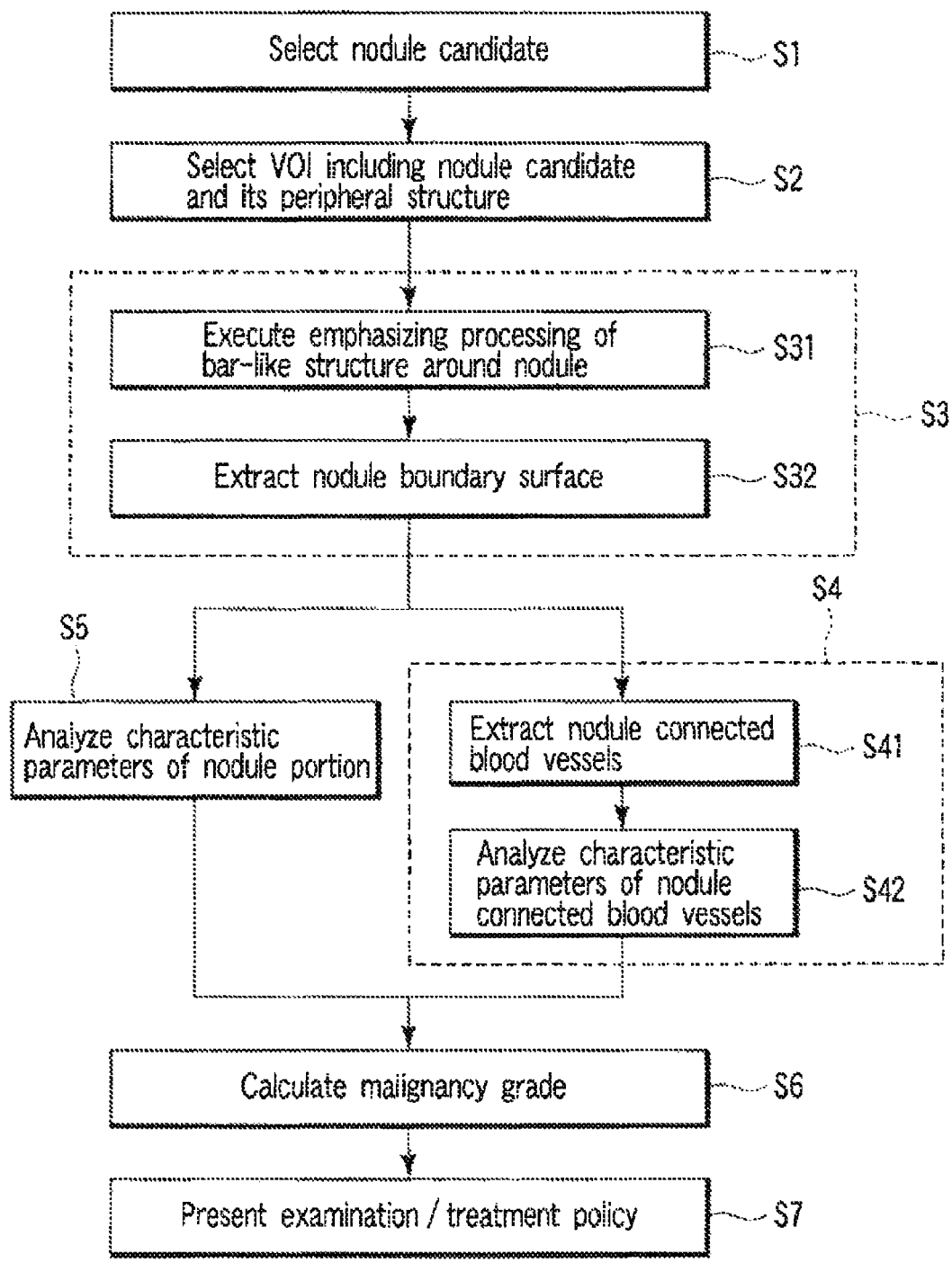
FIG. 2 is a flowchart showing an outline of processing performed to calculate a malignancy grade and determine an examination policy and a treatment policy.

An embodiment will now be explained hereinafter with reference to the accompanying drawings.

FIG. 1 is a view showing a structure of a medical image processing apparatus 1 according to this embodiment.

A processing target of this medical image processing apparatus 1 depicted in FIG. 1 is three-dimensional image data acquired by a multi-slice CT 2. As shown in FIG. 1, the medical image processing apparatus 1 includes a nodule candidate region specifying unit 11, an expanded nodule candidate region specifying unit 12, a determination unit 13, an image data processing unit 14, an image display unit 15, and a policy display unit 16.

This medical image processing apparatus 1 can use, e.g., a general-purpose computer device as basic hardware. Further, the nodule candidate region specifying unit 11, the expanded nodule candidate region specifying unit 12, the determination unit 13, and the image data processing unit 14 can be realized by allowing a processor mounted on the computer device to execute a medical image processing program. At this time, the medical image processing apparatus may be realized by installing the medical image processing program in the computer device in advance, or by recording the medical image processing program in a removable recording medium, e.g., a magnetic disc, a magneto optical disk, an optical disk, or a semiconductor memory or distributing the medical image processing program through a network and installing this medical image processing program in the computer device. It is to be noted that each unit can be also partially or entirely realized by using hardware, e.g., a logic circuit. Furthermore, each of these units can be also realized by combining hardware and software control. As each of the image display unit 15 and the policy display unit 16, a display device, e.g., a CRT (cathode-ray tube) display unit or an LCD (liquid crystal display) can be utilized. Different display devices may be used as the image display unit 15 and the policy display unit 16, respectively. Alternatively, one display device may be used as each of the image display unit 15 and the policy display unit 16 in a time-sharing manner. Alternatively, different regions in a display screen of one display device may be utilized as the image display unit 15 and the policy display unit 16, respectively. It is to be noted that each of the image display unit 15 and the policy display unit 16 can use a general-purpose display device externally provided to the medical image processing apparatus 1 as the image display unit 15 or the policy display unit without being built in the medical image processing apparatus 1.

The nodule candidate region specifying unit 11 specifies a region that can be a nodule (which will be referred to as a nodule candidate region hereinafter) in a three-dimensional image represented by three-dimensional image data. The expanded nodule candidate region specifying unit 12 specifies an expanded nodule candidate region including the nodule candidate region and a peripheral region that is continuous therewith in a three-dimensional image. The determination unit 13 determines whether the nodule candidate region is a nodule based on respective characteristic amounts of the nodule candidate region and the peripheral region. The image data processing unit 14 acquires a malignancy grade of the nodule candidate region based on the respective characteristic amounts of the nodule candidate region and the peripheral region. The image data processing unit 14 further determines an examination policy and a treatment policy based on the determined malignancy grade. Display data required to display a three-dimensional image or display a cross section generated based on image data acquired by the multi-slice CT 2 and the characteristic amounts analyzed by the determination unit 13. It is to be noted that a technique, e.g., volume rendering (which will be referred to as VR hereinafter) is utilized to display a three-dimensional image. Moreover, a technique, e.g., a multi-planar reformation (which will be referred to as MPR hereinafter) method is utilized to display a cross section. Additionally, the image data processing unit 14 generates display data that is required to present the malignancy grade determined by the determination unit 13 and the examination policy and the treatment policy to a user, e.g., a physician. The image display unit 15 displays a three-dimensional image or display a cross section of a medical image based on the display data generated by the image data processing unit 14. The policy display unit 16 performs display to present the malignancy grade, the examination policy, and the treatment policy to a user, e.g., a physician based on the display data generated by the image data processing unit 14.

An operation of the medical image processing apparatus 1 having the above-explained configuration will now be explained.

First, the nodule candidate region specifying unit 11 specifies a nodule candidate region, and the expanded nodule candidate region specifying unit 12 specifies an expanded nodule candidate region. The expanded nodule candidate region includes the nodule candidate region and a peripheral region continuous therewith, and hence the peripheral region is a region excluding the nodule candidate region from the expanded nodule candidate region. The determination unit 13 determines whether the nodule candidate region is a nodule based on characteristic amounts of the nodule candidate region and the peripheral region. A technique disclosed in U.S. patent application Ser. No. 11/736,865 is utilized for the above-explained processing. According to the technique disclosed in U.S. patent application Ser. No. 11/736,865, a foreground portion showing positions of a nodule and a peripheral blood vessel structure/bronchial structure is specified in the above-explained processing, and an ellipsoidal model substantially surrounding the nodule candidate region is generated. It is to be noted that, in this embodiment, the expanded nodule candidate region may be a region larger than a region explained in U.S. patent application Ser. No. 11/736,865.

Further, region information in the nodule candidate region determined to be a nodule by the determination unit 13, region position information, an ellipsoidal model, and foreground portion information showing a nodule and a peripheral blood vessel structure/spicula/bronchial structure, and others may be generated based on the method explained in U.S. patent application Ser. No. 11/758,907 already filed by the present applicants.

It is to be noted that descriptions of U.S. patent application Ser. No. 11/736,865 and U.S. patent application Ser. No. 11/758,907 are incorporated herein by reference.

Subsequently, the image data processing unit 14 executes processing depicted in FIG. 2 with respect to the nodule candidate region determined to a nodule.

FIG. 2 is a flowchart showing an outline of processing for a calculation of a malignancy grade and a determination on an examination policy and a treatment policy.

At a step S, the image data processing unit 14 selects one nodule candidate determined to be a nodule by the determination unit 13.

Figure 3:
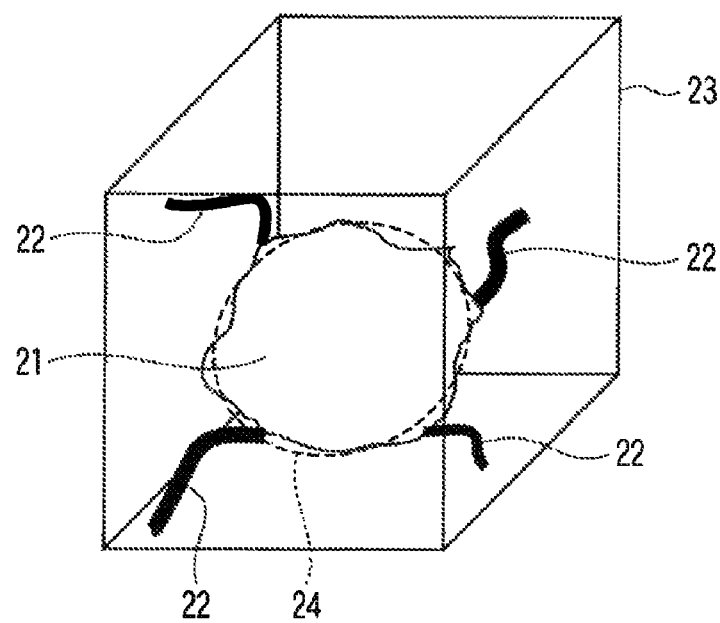
FIG. 3 is a view showing an example of VOI.

At a step S2, the image data processing unit 14 selects a volume of interest (which will be referred to as a VOI hereinafter) 23 including a nodule candidate 21 and its peripheral structure 22 as shown in FIG. 3. Specifically, the determination unit 13 determines a center of an ellipsoidal model 24 generated for the nodule candidate 21 as a center of the VOI 23. Then, a cube having a length which is several fold (e.g., threefold) of an average length or the longest axis of three main axes of the ellipsoidal model 24 as one side thereof is set, and this is determined as the VOI 23. It is to be noted that the VOI may be determined as a spherical body having a length that is several fold (e.g., threefold) of the average length or the longest axis of the three main axes of the ellipsoidal model 24 as a diameter thereof. Furthermore, the image data processing unit 14 extracts image information (an image intensity value) that is placed in the VOI 23 and corresponds to the foreground region from three-dimensional image data. At this time, a region in a lung field where the nodule candidate is placed, i.e., a position in a range extending from a hilar region to a peripheral region where the nodule candidate is placed is calculated from segmented lung region information obtained at a stage before CAD processing.

Figure 4A:
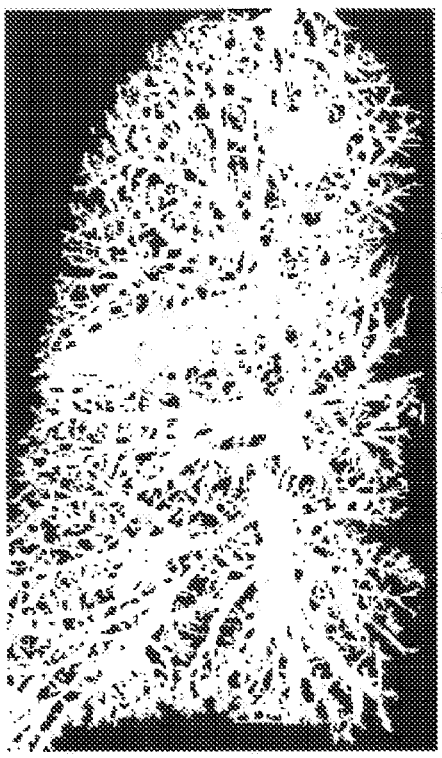
FIGS. 4A and 4B are views showing examples of a foreground region image before executing bar-like structure emphasizing processing and a bar-like structure emphasized image obtained by the emphasizing processing.
Figure 4B:
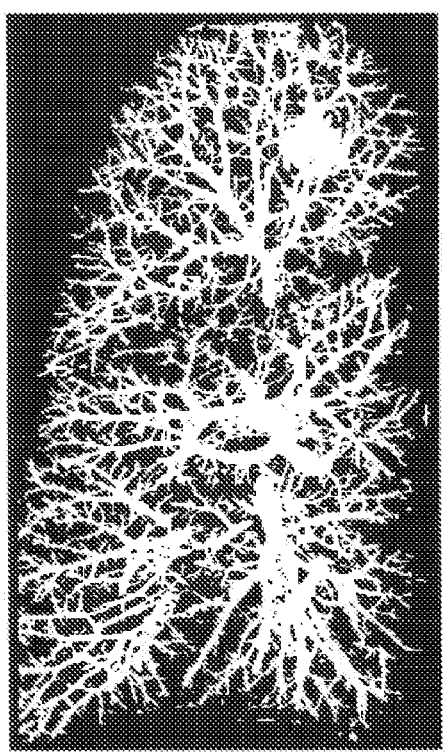

At a step S3, the image data processing unit 14 executes pre-processing at later-explained steps S4 and S5. First, at a step S31, the image data processing unit 14 executes emphasizing processing for each bar-like structure in the VOI 23. That is, as shown in FIG. 4A, the foreground region includes not only blood vessels but also a structure, e.g., a tracheal wall or a lung lobe mesenteriolum. Thus, the image data processing unit 14 generates a bar-like structure emphasized image in which each blood vessel or spicula having a bar-like structure alone is emphasized as shown in FIG. 4B. A known technique called a Hessian filter using an eigen value in a Hessian matrix can be utilized for this emphasizing processing. Alternatively, a given fixed pixel value may be determined as a threshold value to extract a blood vessel or spicula structure so that an obtained image can be used as a bar-like structure emphasized image. It is to be noted that FIGS. 4A and 4B show the foreground region image and the bar-like structure emphasized image in an entire lung, but the processing target at the step S3 is an image corresponding to the foreground region in the VOI alone. However, the emphasizing processing for the bar-like structure may be executed before the step S1 to obtain such a bar-like structure emphasized image as shown in FIG. 4B.

Figure 5A:
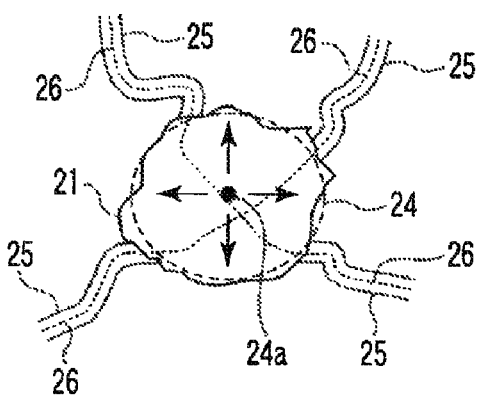
FIGS. 5A, 5B, and 5C are views for explaining extracting processing for a nodule boundary surface and bar-like connected structures.
Figure 5B:
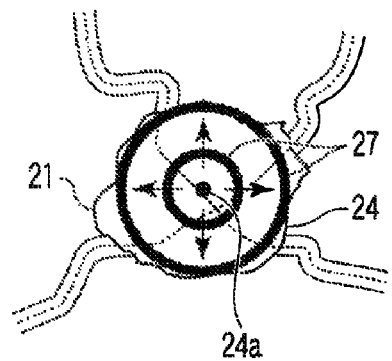
Figure 5C:
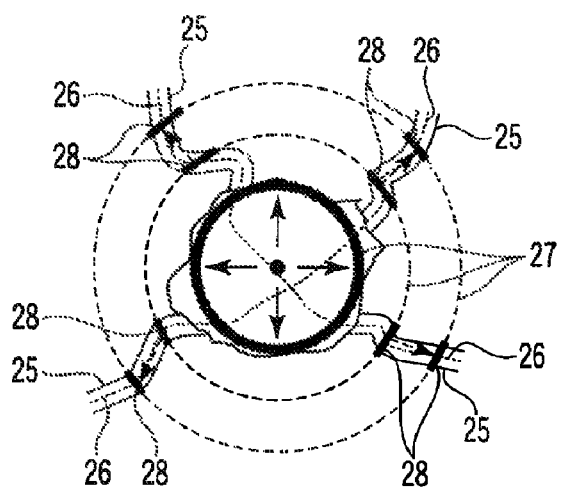

Then, at a step S32, the image data processing unit 14 extracts a nodule boundary surface. Specifically, as shown in FIG. 5A, the image data processing unit 14 first uses a distance conversion method with respect to the nodule candidate 21 and each bar-like structure 25 that appear in the bar-like structure emphasized image to obtain a central line 26 as a line connecting maximum values of distance converted images obtained by this method. Subsequently, the image data processing unit 14 uses a region extension method in a three-dimensional spherical shape from a center of the nodule candidate, i.e., a center 24a of the ellipsoidal model 24 in the bar-like structure emphasized image as shown in FIG. 5A to extract a boundary of the nodule candidate 21 as depicted in FIG. 5B. In sequential extension of a surface of the spherical region (which will be referred to as a spherical surface hereinafter) 27, when a rate of change in a intensity value of this spherical surface 27 exceeds a given threshold value, this point is recognized as the boundary as shown in FIG. 5B. As a result of the above-explained processing, since the nodule candidate can be separated from the bar-like structure as a blood vessel, a boundary surface representing the nodule candidate portion alone is obtained. Thus, the image data processing unit 14 uses this boundary surface to obtain a shape or a volume of the nodule candidate.

Figure 6:
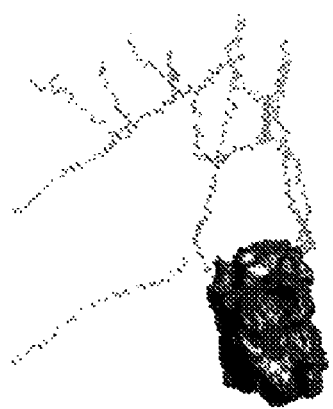
FIG. 6 is a view showing an extraction example of a nodule and nodule connected blood vessels.

At a step S4, the image data processing unit 14 analyzes a characteristic parameter of the bar-like structure connected with the nodule (which will be referred to as a bar-like connected structure hereinafter). Specifically, at a step S41, the image data processing unit 14 first detects each portion (which will be referred to as a spherical small region hereinafter) 28 that overlaps the bar-like structure 25 and includes a central line 26 in the spherical surface 27. Then, the spherical small region 28 is detected while sequentially extending the spherical surface 27 to track the bar-like connected structure. Although the bar-like connected structure is a spicula that can be regarded as a blood vessel or a part of the nodule, the blood vessel is identified from a length of the bar-like connected structure by utilizing knowledge that a length of the spicula is not greater than 2 cm. In this manner, a nodule connected blood vessel connected with the nodule is extracted. FIG. 6 shows an example of extracting the nodule and nodule connected blood vessels.

Figures 7, 8:
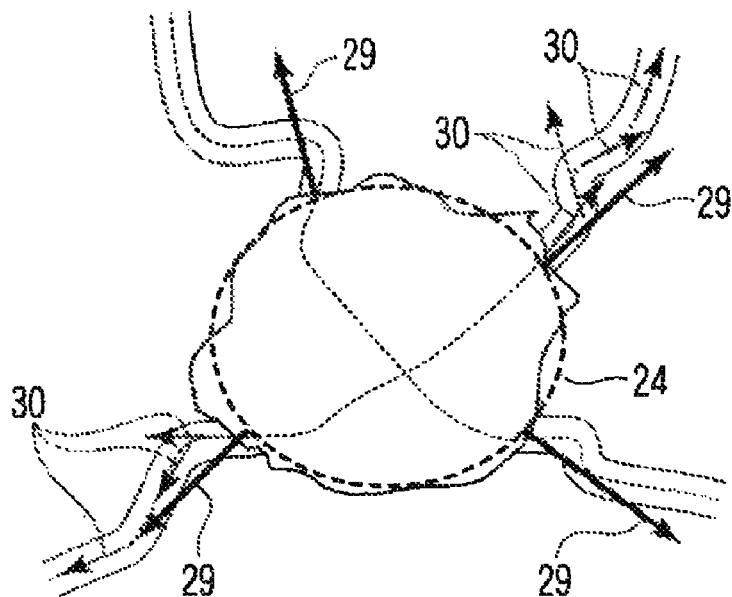
FIG. 7 is a view showing an example of normal vectors and directional vectors.
FIG. 8 is a view showing an example of a correspondence table for a malignancy grade, an examination policy, and a treatment policy.

Then, at a step S42, the image data processing unit 14 analyzes the number of nodule connected blood vessels and an amount indicative of a connection angle of each nodule connected blood vessel with respect to the nodule as characteristic parameters. It is to be noted that the connection angle of each nodule connected blood vessel with respect to the nodule approximates an angle of the nodule connected blood vessel with respect to a curved surface of the ellipsoidal model. Thus, as shown in FIG. 7, an intersection of the ellipsoidal model surface and each central line 26 is determined as a base point, and the image data processing unit 14 analyzes an inner product value of each normal line vector 29 extending outwardly from the nodule candidate with respect to an ellipsoidal tangential surface at the base point and a directional vector at each point on each central line 26 of the nodule connected blood vessel as a characteristic parameter. Further, if the characteristic parameter changes from a past image, this change is also analyzed as a characteristic parameter.

At a step S5, the image data processing unit 14 analyzes the characteristic parameters of the nodule portion. Specifically, the image data processing unit 14 uses information of the nodule boundary surface obtained at the step S32 to analyze a volume of the nodule, spherical shape properties (also called compactness) of the same, the number of spicula that can be regarded as a part of the nodule identified from the bar-like structures, a histogram pattern of a intensity value (e.g., an HU value) in the nodule, and others as the characteristic parameters. Furthermore, if these characteristic parameters change from a past image, this change is also analyzed as a characteristic parameter.

At a step S6, the image data processing unit 14 uses the plurality of characteristic parameters obtained at the steps S4 and S5 to calculate a degree of malignancy/benignancy, i.e., a malignant grade of the nodule candidate. Specifically, the image data processing unit 14 uses the plurality of characteristic parameters obtained at the steps S4 and S5 as input values, and makes a comprehensive determination on a malignant grade of the nodule based on an existing neural network technique or a supervised neural network model to represent the malignant grade as a numerical value. As the supervised neural network model, a support vector machine (SVM) (see C. J. C. Burges, "A Tutorial on Support Vector Machines for Pattern Recognition", Data Mining and Knowledge Discovery 2:121-167, 1998) can be utilized. Moreover, as a tutorial value, e.g., a threshold value of the characteristic parameter indicative of the known malignant grade can be utilized. Alternatively, the characteristic parameters can be classified into categories each representing a malignant grade, e.g., a characteristic parameter related to the nodule connected blood vessel (which will be referred to as a connected structure group characteristic parameter hereinafter) and a characteristic parameter related to the nodule portion (which will be referred to as a nodule group characteristic parameter hereinafter) to provide a numerical value indicative of each malignancy grade. Additionally, a numerical value of the characteristic parameter itself can be used as a malignancy grade.

At a step S7, the image data processing unit 14 presents an examination policy and a treatment policy based on a numerical value indicative of a malignant grade alone or a combination of, e.g., the plurality of extracted characteristic parameters and positional information in a lung field of the nodule candidate. The examination policy and the treatment policy can be stylized in compliance with a guideline already reported from, e.g., an academic conference, or they may be customized in accordance with each facility. As the guideline, there are those reported in literary documents, e.g., Daniel M. Libby and five others, "Managing the Small Pulmonary Nodule Discovered by CT", Chest, Vol. 125, No. 4, 2004, pp. 1522-1529, Herber MacMahon and seven others, "Guidelines for Management of Small Pulmonary Nodules Detected on CT Scans: A statement from the Fleischner Society", Radiology, Vol. 237, No. 2, 2005, pp. 395-400, and others. Specifically, the image data processing unit 14 uses the malignant grade obtained at the step S6 to present an examination policy and a treatment policy based on such a correspondence table as depicted in FIG. 8 in case of, e.g., the single malignant grade. Alternatively, in case of the malignant grades using the plurality of parameter groups (in this example, the parameters are classified into characteristic parameters related to the nodule connected blood vessel and characteristic parameters related to the nodule portion), the image data processing unit 14 selects and presents an examination policy and a treatment policy based on such a matrix relationship table as shown in FIG. 9. Further, the image data processing unit 14 may select and present an examination policy and a treatment policy from a multidimensional matrix relationship table showing numerical values of the characteristic parameters themselves as malignant grades. Furthermore, for example, a neural network technique may be utilized to determine an examination policy and a treatment policy without selecting these policies from the correspondence table or the matrix relationship table.

As explained above, according to this embodiment, since the malignant grade of the nodule candidate is calculated while considering not only characteristics of the nodule candidate but also characteristics of its peripheral region, the malignant grade can be appropriately determined as compared with an example where characteristics of the nodule candidate alone are considered. Further, according to this embodiment, since the examination policy and the treatment policy are presented based on the thus determined malignant grade, appropriate diagnosis conforming to a scientific basis can be performed without being dependent on a difference in experience or opinion between physicians.

Moreover, according to this embodiment, an inner product value of the normal line vector 29 and the directional vector 30 is considered to calculate a malignant grade. This inner product value is increased when an angle of the nodule connected blood vessel with respect to the curved surface of the ellipsoidal model becomes close to a perpendicularity. Since a malignant nodule pulls in a blood vessel, the blood vessel is substantially vertically connected with the nodule. Additionally, the nodule pulls in the blood vessel from a farther position as a malignant grade becomes high. Therefore, in regard to the blood vessel connected with the nodule having a high malignant grade, the directional vector 30 has a direction similar to that of the normal vector 29 at not only a point close to the nodule but also a point apart from the nodule. That is, in case of a nodule having a high malignancy grade, the inner product value is further increased. Therefore, the inner product value is information very useful to judge a malignant grade of the nodule, and considering such information enables further appropriately judging the malignant grade (see Yasushi Hirano and five others, "Quantification using Three-dimensional Concentration Ratio of Vascular/Bronchial Convergence in Chest X-ray CT Image", MEDIAL IMAGING TECHNOLOGY Vol. 15, No. 3, 1997, pp. 228-236).

Further, since the inner product value varies in accordance with a malignant grade in this manner, paying attention to a change in the inner product value with time enables appropriately judging a degree of aggravation of the nodule.

Furthermore, according to this embodiment, since the normal vector 29 is set with the ellipsoidal model 24 being determined as a reference, the normal vector 29 that is appropriate to analyze a connecting direction of a blood vessel can be readily set even if a surface of the nodule candidate is not smooth.

This embodiment can be modified in many ways as follows.

(1) As shown in FIG. 10, a technique, e.g., a neural network or a tutorial neural network model may be utilized to directly determine presentation contents of an examination policy and a treatment policy from one or more nodule group characteristic parameters and one or more connected structure group characteristic parameters.

(2) Although the characteristic parameter concerning the nodule and the characteristic parameter concerning the connected structure are numerical information that is analyzed in a given examination, individually observing a change in the respective characteristic parameters with time is also important to further accurately determine a malignant grade.

Figure 11:
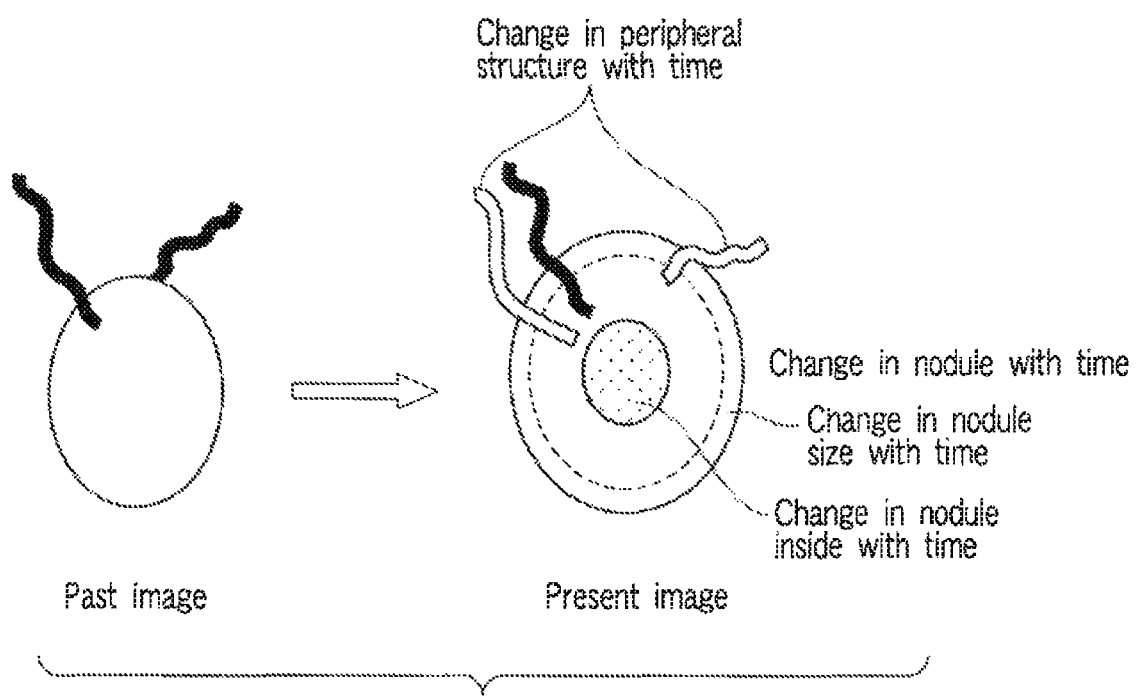
FIG. 11 is a view showing an example of how a nodule or a peripheral structure varies with time.

Thus, a correspondence between a branch point of a main branch and that of a first branch of a bronchial tube which can necessarily achieve a correspondence with respect to a past image and a present image as an entire lung field is determined. This result is determined as a reference, and land marks of peripheral branches of a bronchial tube or those of branch points of a blood vessel are associated with each other, to effect positioning and the corresponding past image and present image are registered including image distortion correction. Then, as shown in FIG. 11, a change in the nodule with time or a change in the peripheral structure with time in the past image and the present image is calculated.

For example, a size of the nodule or a change in an internal structure of the nodule that is most important in a change in the nodule with time is extracted from a difference image, and it is recorded as a change in the characteristic parameter or new generation of a characteristic parameter. As to a change in the peripheral structure with time, an increase or a decrease in the number of characteristic parameters is recorded as an index, e.g., new occurrence of a spicula.

Figure 12:
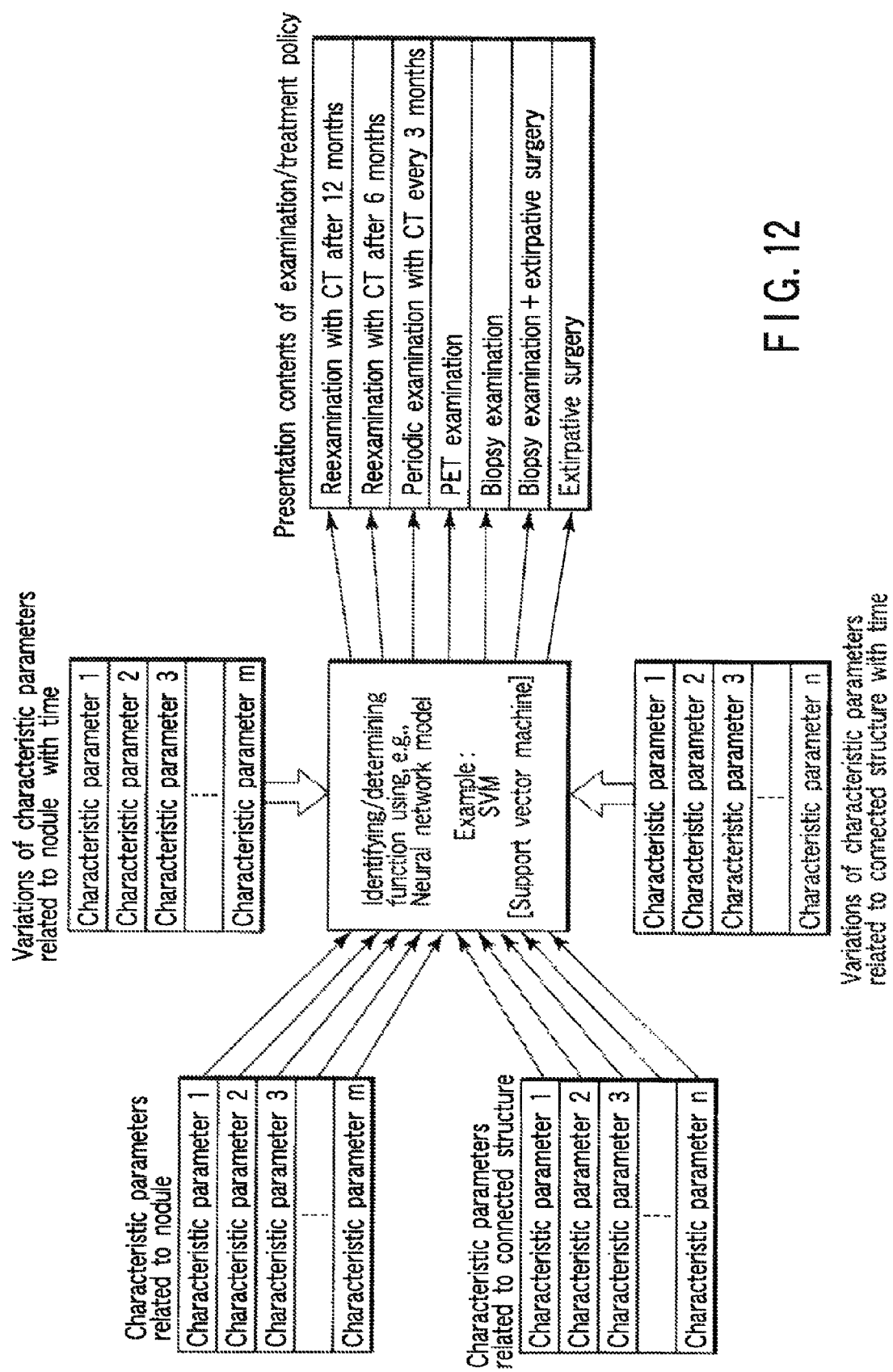
FIG. 12 is a view showing a modification of the determination processing for an examination policy or a treatment policy.

The parameters used in an examination and a change in the characteristic parameters as a change with time (e.g., a change in a numerical value like a size or a change in the number of the characteristics parameters like spicula) are input, and a technique, e.g., a neural network or a supervised neural network model may be utilized to directly determine presentation contents of the examination policy and the treatment policy as shown in FIG. 12.

(3) Presenting the examination policy and the treatment policy based on a malignant grade calculated like a conventional example without considering the inner product value is also effective.

(4) One of the examination policy and the treatment policy may be determined or presented.

(5) Although a three-dimensional image acquired by the multi-slice CT 2 is a processing target in each foregoing embodiment, a three-dimensional image collected by using any other diagnosis modality, e.g., an X-ray diagnostic apparatus, a magnetic resonance diagnostic apparatus, or an ultrasound diagnostic apparatus may be a processing target.

(6) A nodule candidate region specified by a user may be judged instead of automatically selecting a nodule candidate region at the step S1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image processing apparatus comprising:
an acquisition unit which acquires an anatomical malignant grade of an abnormality candidate region that is possibly an anatomical abnormality included in an image showing the inside of a subject based on a candidate region characteristic amount indicative of characteristics concerning the abnormality candidate region and a peripheral region characteristic amount indicative of characteristics concerning a peripheral region continuous with the abnormality candidate region in the image;
a determination unit which determines an examination policy or a treatment policy with respect to the abnormality candidate based on the malignancy grade; and
a presentation unit which presents the examination policy or the treatment policy determined by the determination unit to a user.

2. The medical image processing apparatus according to claim 1, further comprising:
a first specification unit which specifies the abnormality candidate region in the image;
a second specification unit which specifies the peripheral region in the image;
a first calculation unit which calculates the candidate region characteristic amount; and
a second calculation unit which calculates the peripheral region characteristic amount.

3. The medical image processing apparatus according to claim 2, wherein the first calculation unit calculates at least one of a shape and a size of the abnormality candidate region as the candidate region characteristic amount from image intensity in the abnormality candidate region.

4. The medical image processing apparatus according to claim 2, wherein the second calculation unit calculates a characteristic amount about a bar-like structure that is included in the peripheral region and connected with the abnormality candidate region as the peripheral region characteristic amount.

5. The medical image processing apparatus according to claim 4, wherein the second calculation unit calculates at least one of a size and a shape of the bar-like structure and a connection angle of the same with respect to the abnormality candidate region as the peripheral region characteristic amount.

6. The medical image processing apparatus according to claim 5, wherein the connection angle is calculated as an inner product value of a normal vector with respect to an ellipsoidal model surface substantially surrounding the abnormality candidate region and a directional vector of a central line of the bar-like structure at each of several points on the central line.

7. The medical image processing apparatus according to claim 2, wherein the second calculation unit calculates a characteristic amount indicative of a degree of a change in characteristics of the peripheral region with time as the peripheral region characteristic amount.

8. The medical image processing apparatus according to claim 2, wherein the first calculation unit calculates a characteristic amount indicative of a shape type and a size of the abnormality candidate region and a degree of a change in the abnormality candidate region with time as the peripheral region characteristic amount, the second calculation unit calculates a characteristic amount indicative of characteristics of a bar-like structure that is included in the peripheral region and connected with the abnormality candidate region and a change in characteristics of the peripheral region with time as the peripheral region characteristic amount, and the acquisition unit acquires the malignant grade based on the shape type and the size of the abnormality candidate region and the degree of a change in characteristics of the abnormality candidate region with time calculated by the first calculation unit, and the characteristics of the bar-like structure included in the peripheral region and connected with the abnormality candidate region and the degree of a change in characteristics of the peripheral region with time calculated by the second calculation unit.

9. The medical image processing apparatus according to claim 1, wherein the determination unit determines at least one of an examination type, a period until the next examination, and a treatment type based on the malignant grade.

10. A medical image processing method comprising:

acquiring an anatomical malignant grade of an abnormality candidate region that is possibly an anatomical abnormality included in an image showing the inside of a subject based on a candidate region characteristic amount indicative of characteristics concerning the abnormality candidate region and a peripheral region characteristic amount indicative of characteristics concerning a peripheral region continuous with the abnormality candidate region in the image;

determining an examination policy or a treatment policy with respect to the abnormality candidate based on the malignant grade; and presenting the determined examination policy or treatment policy to a user.

* * * * *